United States Patent [19]

Haas et al.

[11] Patent Number: 5,504,254
[45] Date of Patent: Apr. 2, 1996

[54] PROCESS FOR THE PREPARATION OF ISOPHORONEDIAMINE

[75] Inventors: Thomas Haas, Frankfurt; Dietrich Arntz, Oberursel; Dieter Most, Bruchkoebel, all of Germany

[73] Assignee: Degussa Aktiengesellschaft, Frankfurt, Germany

[21] Appl. No.: 361,383

[22] Filed: Dec. 22, 1994

[30] Foreign Application Priority Data

Dec. 22, 1993 [DE] Germany ............... 43 43 890.3

[51] Int. Cl.$^6$ ............................................. C07C 209/22
[52] U.S. Cl. ................. 564/446; 564/445; 564/448; 564/461
[58] Field of Search ................... 564/461, 448, 564/455, 445, 446

[56] References Cited

U.S. PATENT DOCUMENTS

| | | | |
|---|---|---|---|
| 3,352,913 | 11/1967 | Schmitt et al. | 260/563 |
| 4,419,337 | 12/1983 | Jagodzinskl et al. | 423/574 R |
| 4,429,157 | 1/1984 | Disteldorf et al. | 564/446 |
| 5,091,554 | 2/1992 | Huthmacher et al. | 558/341 |

FOREIGN PATENT DOCUMENTS

| | | |
|---|---|---|
| 2093374 | 7/1993 | Canada. |
| 0042119 | 12/1981 | European Pat. Off.. |
| 0394967 | 10/1990 | European Pat. Off.. |
| 0449089 | 10/1991 | European Pat. Off.. |
| 3011656 | 10/1981 | Germany. |
| 3942371 | 5/1992 | Germany. |

OTHER PUBLICATIONS

SRI International Report No. 1D, "Isocyanates", Supplement D, by Yu–Ren Chin (Jul. 1983).
auf der Heyde, W., et al., Die Angewandte Makromolekulare Chemie 153 (1987) 1–13, No. 2502.
CA 118:101555v (1993, Feb.).

*Primary Examiner*—Allen J. Robinson
*Attorney, Agent, or Firm*—Beveridge, DeGrandi, Weilacher & Young

[57] ABSTRACT

A process is disclosed for the continuous preparation of 3-aminomethyl-3,5,5-trimethylcyclohexylamine (isophoronediamine) in high yield and high purity from 3-cyano-3,5,5-trimethylcyclohexanone (isophoronenitrile) by aminating hydrogenation with hydrogen and ammonia in the presence of a fixed bed catalyst. The aminating hydrogenation is carried out by allowing a mixture of isophoronenitrile, ammonia and a $C_1$–$C_3$–alcohol, in the presence of hydrogen, to trickle over a trickle bed reactor provided with a Co and/or Ru fixed bed catalyst, at 3 to 8 MPa and at a temperature of 40° to 150° C., preferably 90 to 130° C., and working up the reaction mixture by distillation. Preferably, a high-boiling by-product fraction, containing a bicyclic amidine, is added to the mixture to be hydrogenated, thereby appreciably increasing the yield.

45 Claims, 1 Drawing Sheet

PROCESS FOR THE PREPARATION OF ISOPHORONEDIAMINE

INTRODUCTION AND BACKGROUND

The present invention relates to a process for the preparation of 3-aminomethyl-3,5,5-trimethylcyclohexylamine, hereafter also called isophoronediamine or abbreviated as IPDA, from 3-cyano-3,5,5-trimethylcyclohexanone, hereafter also called isophoronenitrile or abbreviated as IPN, by an aminating hydrogenation reaction with hydrogen and ammonia in the presence of a fixed bed catalyst. The process according to the present invention affords the continuous preparation of isophoronediamine in high yield and high purity.

Isophoronediamine is used as a starting material for the preparation of isophorone diisocyanate, which is used as an isocyanate component for polyurethane systems, as an amine component for polyamides, and as a hardener for epoxy resins. Isophoronediamine is conventionally prepared from isophoronenitrile, the carbonyl group being converted to an amino group and the nitrile group to an aminomethyl group in the presence of ammonia, hydrogen and conventional hydrogenation catalysts. The starting material, isophoronenitrile, can be obtained in a conventional manner by the addition of hydrogen cyanide onto isophorone (see U.S. Pat. No. 5,091,554 which is incorporated by reference in its entirety; DE-OS 39 42 371).

According to the process described in U.S. Pat. No. 3,352,913 (which is incorporated by reference in its entirety) for the preparation of isophoronediamine from isophoronenitrile, the hydrogenation is carried out in the presence of ammonia and in the presence of cobalt-, nickel-, iron- or noble metal-containing catalysts known per se, at 50° to 150° C. and at a pressure of at least 5 MPa. By way of example, the hydrogenation takes place in the presence of methanol as a solvent. Apart from the desired isophoronediamine, by-products, such as 3-aminomethyl-3,5,5-trimethylcyclohexanol (isophoroneamino alcohol, abbreviated as IPAA) in particular, are formed in relatively large amounts. The disadvantages of this process are found to be the low yield and a considerable proportion of by-products.

In the quest to obtain a higher yield of IPDA and minimize the unavoidable formation of IPAA, DE-OS 30 11 656 teaches a two-step process; in the first step, IPN is converted with excess ammonia, without a catalyst, to 3-cyano-3,5,5-trimethyliminocyclohexane which is hydrogenated in the second step to IPDA. The disadvantage of this process is that, as well as the actual hydrogenation reactor, a special imine formation reactor is required.

EP-B 0 042 119 (U.S. Pat. No. 4,429,157) proposes a further improvement to the process of producing IPDA, wherein, prior to reaction with ammonia and hydrogen in the presence of hydrogenation catalysts at temperatures of 10° to 120° C. and pressures of 0.1 to 30 MPa, the isophoronenitrile is subjected to a preliminary reaction with ammonia in the presence of inorganic and organic ion exchangers in the ammonium form as imine formation catalysts. Whereas the volume ratio of isophoronenitrile to ammonia in the imine (isophoroneimine or Schiff's base) formation step is said to be 1:0.5 to 20, this ratio is increased to 1:10 to 20 in the hydrogenation step. The economy of the process is compromised by the use of two different catalysts and the large excess of ammonia, which necessitates a very high pressure and hence an expensive hydrogenation apparatus.

EP-B 0 042 119 also discloses a Comparative Example in which isophoronenitrile and liquid ammonia are pumped into the top of a hydrogenation reactor charged with commercially available cobalt catalyst. The reaction system is kept at 270 bar with $H_2$; a certain gas stream is set up and a certain amount of off-gas is withdrawn. The reaction mixture leaving the bottom of the reactor is then worked up by distillation. Despite approximately quantitative conversion of the isophoronenitrile, this embodiment produces only 48% of isophoronediamine, together with many by-products. EP-B 0 042 119 does not suggest passing a mixture containing isophoronenitrile, ammonia and organic solvent, instead of a mixture of isophoronenitrile and ammonia, over a trickle bed reactor at an essentially low pressure and without the need for a preliminary imine formation reaction.

EP-A 0 449 089 (CA 2,039,328) discloses another process for the preparation of isophoronediamine. In two spatially separated reaction chambers, a solution of isophoronenitrile in tetrahydrofuran is initially reacted with excess ammonia on acidic metal catalysts to form 3-cyano-3,5,5-trimethylcyclohexylimine and the reaction mixture is hydrogenated at high pressure in a second reaction chamber with hydrogen in the presence of excess ammonia on catalysts containing cobalt, nickel, ruthenium and/or other noble metals, and optionally basic components. By way of example, the mixture leaving the first reaction step is passed through the hydrogenation reactor from bottom to top; the reactor is operated as a bubble reactor. EP-A 0 49 089 does not give any indication of also using the reactor as a trickle bed reactor and directly feeding said reactor with a mixture of isophoronenitrile, ammonia and an organic solvent.

EP-A 0 394 967 teaches a process for the amination of carbonylnitriles and iminonitriles and also includes the preparation of isophoronediamine from isophoronenitrile. The starting material is initially converted to the aminonitrile at moderate temperatures under conditions of reductive amination, i.e. in the presence of hydrogen, ammonia and a hydrogenation catalyst; the nitrile group is then converted to an aminomethyl group at elevated temperature in the presence of a hydrogenation catalyst which is effective in the hydrogenation of nitrile groups. Although this process can be carried out at low pressures, the fact that a strictly observed temperature program has to be operated during both the reaction steps is regarded as a considerable disadvantage since it results in an appreciable lowering of the space-time yield and hence the economy of the process. In addition, unless special promoters are also used, the product quality does not satisfy the requirements of low by-products because the content of 3-cyano-3,5,5-trimethylaminocyclohexane, which cannot be separated off by distillation, is usually too high.

According to JP-A-4-300852, a pressure reduction in the preparation of isophoronediamine by the aminating catalytic hydrogenation of isophoronenitrile is also made possible by carrying out the hydrogenation in the presence of a supported ruthenium catalyst. However, JP-A-4-300852 refers only to conditions for suspension hydrogenation and not to conditions using a fixed bed reactor.

SRI International Report No. 1D, "Isocyanates" by YUREN CHIN (July 1983), gave a survey of an industrial process for the preparation of isophoronediamine from isophoronenitrile. In the process described therein, a mixture of isophoronenitrile, methanol and ammonia is passed with hydrogen over a fixed bed reactor containing a supported catalyst of cobalt-on-kieselguhr. In the embodiment described, the catalyst bed is always flooded (bubble column). The operating pressure is given as 150 bar. Also, hydrogen is used in excess and, after the reaction, this excess must be separated from the reaction mixture, purified, compressed and then recycled. The economy of this process is reduced both by the high operating pressure and by the technical cost of recycling the hydrogen. As established in comparative Example 3b below, this embodiment results in the increased formation of by-products which cannot easily be separated off, and to a lowering of the yield.

SUMMARY OF THE INVENTION

One object of the present invention is to mitigate the disadvantages of the previously known processes for the preparation of isophoronediamine from isophoronenitrile using a reactor charged with a fixed bed catalyst, to the effect that the economy of the process is increased. In particular, the cost of the technical equipment should be reduced compared with the previously known processes. It should moreover be possible to obtain isophoronediamine in high yield and to isolate it from the reaction mixture in very pure form by means of conventional distillative measures.

According to the present invention, isophoronediamine is prepared from a mixture of isophoronenitrile, an organic solvent, and ammonia which is hydrogenated with hydrogen at a pressure sufficient to enable hydrogen to be transported through the liquid to the catalyst surface, in the presence of at least one hydrogenation catalyst, and the isophoronediamine is recovered from the reaction mixture by distillation. The aminating hydrogenation is carried out in a trickle bed reactor, the mixture of isophoronenitrile, organic solvent and ammonia being charged onto the catalyst bed at the top end of the reactor, and the reaction mixture obtained after trickling through the catalyst bed being withdrawn at the bottom end of the reactor.

BRIEF DESCRIPTION OF THE DRAWING

The present invention will be further understood with reference to the drawing, wherein:

FIG. 1-(b) is a schematic representation of trickle bed reactors connected in series.

DETAILED DESCRIPTION OF THE INVENTION

According to a more detailed aspect of the present invention, isophoronediamine is prepared from a mixture of isophoronenitrile, an organic solvent (e.g., lower alkyl alcohol), and ammonia which is hydrogenated with hydrogen at a pressure sufficient to enable hydrogen to be transported through the liquid to the catalyst surface (e.g., in the range 3 to 10 MPa) and at a temperature in the range 80° to 150° C. in the presence of at least one hydrogenation catalyst from the group comprising cobalt and/or ruthenium fixed bed catalysts, and the isophoronediamine is recovered from the reaction mixture by distillation. The aminating hydrogenation is carried out in a trickle bed reactor, the mixture of isophoronenitrile, organic solvent and ammonia being charged onto the catalyst bed at the top end of the reactor, and the reaction mixture obtained after trickling through the catalyst bed being withdrawn at the bottom end of the reactor.

Figure 1A:
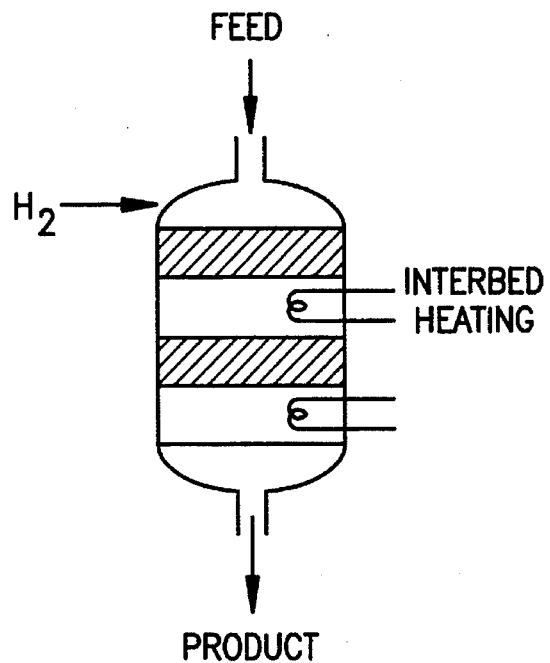
FIG. 1-(a) is a schematic drawing showing a trickle bed reactor which can contain one or more layers of fixed bed catalyst.
Figure 1B:
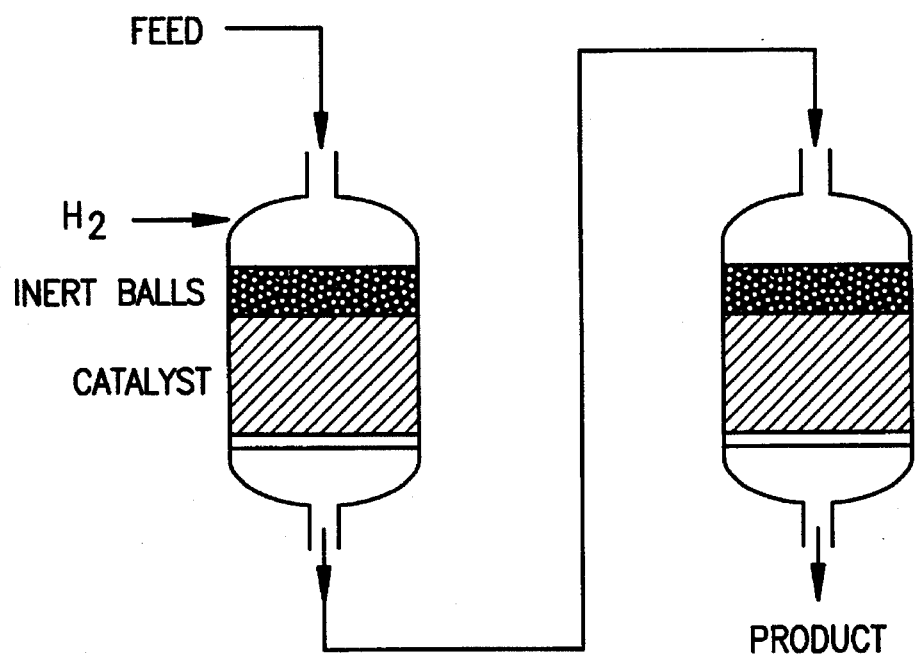

The reaction according to the present invention is carried out in a conventional trickle bed reactor. The designs of such reactors are known to those skilled in the art. The fixed bed catalyst is arranged in the form of one or more layers in a container; the reactor is also equipped with devices for thermostating the catalyst layers in order to control the heat and to ensure that the desired temperature is maintained in the respective catalyst layer (see FIG. 1a). As an alternative to a single trickle bed reactor, several trickle bed reactors can be connected in series, the reaction mixture leaving the first reactor being recharged into the top of the second reactor and so on (FIG. 1b). The trickle bed reactor or reactors are also equipped with suitable devices for charging the reactants (i.e., in this case the mixture containing isophoronenitrile, ammonia and solvent, and the hydrogen) as well as with devices for distributing the liquid over the surface of the first catalyst bed and, finally, with suitable devices for discharging the reaction mixture leaving the reactor. Such equipment is well known in the art, see for example Kirk-Other's *Encyclopedia of Chemical Technology*, Third Edition, Volume 19, pages 880–914 (this excerpt is entirely incorporated herein by reference), especially page 884.

An essential feature of the process according to the present invention is that the reaction mixture to be hydrogenated trickles over the catalyst bed and also that a sufficiently large gas volume exists within the catalyst bed to enable the hydrogen to be transported through the liquid film onto the catalyst surface. It has been found that the trickle bed process is substantially and surprisingly responsible for obtaining a high product yield and, in particular, a high selectivity. As used herein, "sufficiently large gas volume" means at least 50% of the volume of the catalyst particles; the "gas volume" is the space between the catalyst particles (approximately pellets) and is inclusive of the pore volume of the catalyst particles.

The yield in the present process with recycling of the high boiling (amidine containing) fraction lies preferably between greater than 91% and 95%; without recycling of the high boiling fraction, the yield most often lies between about 87% and 90% (preferably 87%–90%). The purity of the products lies in general above 99.6% preferably between 99.7 and 99.9%

If the reactor is operated not as a trickle bed reactor (where the liquid flows as a continuous film over the catalyst; the liquid mixture is allowed to trickle over the catalyst bed in the presence of hydrogen) but as a bubble reactor, in which case the catalyst bed is always flooded (the liquid reaction mixture is conveyed from bottom to top so that the reactor is always flooded), a considerably lower yield of isophoronediamine is obtained under otherwise identical reaction conditions with respect to temperature, pressure and concentration of the reactants; the bubble process also gives a different range of by-products, methylisophoronediamine (methyl-3-aminomethyl-3,5,5-trimethylcyclohexylamine) being formed in particular. Methylisophoronediamine cannot be separated from isophoronediamine by distillation under conventional conditions, so the formation of such by-products must already be avoided in the preparation of the isophoronediamine crude product. Surprisingly, such by-products are only formed in very small amounts under the conditions of the process according to the present invention. A further disadvantage of the bubble process is that hydrogen has to be added in excess in order to achieve saturation of the solution with $H_2$; this entails expensive recycling of the excess $H_2$.

When the process according to the present invention is carried out, hydrogen can be fed into the reactor either in excess or in an amount such that no hydrogen has to be discharged from the reactor and recycled. The introduction of hydrogen in excess is less preferable because the technical cost of separating off the excess $H_2$, condensing ammonia and organic solvent contained in the discharged hydrogen, and compressing the purified hydrogen and recycling it is considerable and reduces the economy of the process on account of the higher investment demanded. Moreover, an even lower yield of IPDA has been found compared with the process not using excess $H_2$. Thus, hydrogen is preferably introduced not in excess but only in the amount which is required to maintain the desired operating pressure.

The aminating hydrogenation reaction is carried out at a pressure in the range 3 to 10 MPa, preferably at 5 to 8 MPa. Such moderate operating pressures, which are possible when using the mixtures of isophoronenitrile, ammonia and solvent and the trickle bed process under the temperature conditions according to the present invention, increase the economy, compared with processes which demand a high operating pressure, by lowering the level of investment required for the apparatus.

The requisite volume of fixed bed catalyst is governed by the LHSV value (liquid hourly space velocity which is dependent on the operating pressure, the temperature and the catalyst activity) which must be observed in order to achieve a quantitative conversion of isophoronenitrile. Generally, the LHSV value is 0.5 $h^{-1}$ or preferably above. The LHSV value is preferably between 0.8 and 1.5 $h^{-1}$; it is particularly good to attain an LHSV value in this range when the reaction is carried out at a temperature in the range between 90° and 130° C. and at a pressure of between 5 and 8 MPa.

In addition to the above mentioned parameters of pressure, temperature and catalyst activity, the LHSV value is also influenced by the chosen concentration ratios of isophoronenitrile, ammonia and solvent and by the type of solvent used. The mixture charged onto the catalyst bed conveniently contains 10 to 40% by weight and preferably 10 to 30% by weight of isophoronenitrile and 10 to 40% by weight and preferably 20 to 40% by weight of ammonia. Organic solvents which can be used are lower alkyl alcohols such as methanol, ethanol, n-propanol and isopropanol. Methanol is the preferred solvent. These solvents are inert to the reaction. The isophoronenitrile, ammonia and solvent are mixed in proportions such that an essentially homogeneous solution results. In principle, it is also possible to fall short of or exceed the above mentioned limiting values for ammonia and isophoronenitrile provided a homogeneous solution results. The use of a mixture containing less than 10% by weight of isophoronenitrile has an adverse effect on the economy of the process.

Apart from the constituents mentioned above, the mixture to be charged onto the catalyst can contain fractions, boiling above or below isophoronediamine, from the distillative recovery of the reaction mixture withdrawn from the trickle bed reactor. In addition to isophoronediamine residues, such fractions can also contain by-products from which isophoronediamine is re-formed under the reaction conditions. The yield of isophoronediamine can be markedly increased by recycling such fractions into the mixture to be used. It is particularly advantageous to feed the fraction boiling after the isophoronediamine, which, in addition to isophoronediamine residues, contains 3,5,5-trimethyl-6-imino-7-azabicyclo[3,2,1]octane as the main product, into the trickle bed reactor together with the mixture of isophoronenitrile, ammonia and solvent. Recycling of the fraction containing the 3,5,5-trimethyl-6-imino-7-azabicyclo[3,2,1]octane, a bicyclic compound of amidine structure, makes it possible to significantly increase the yield of isophoronediamine and consequently to improve the economy of the process.

The catalysts to be used according to the present invention are cobalt and/or ruthenium fixed bed catalysts; these catalysts are conventionally in the form of pellets, extrudates or other moldings known in the art. It is particularly convenient to use supported catalysts, cobalt or ruthenium being present on a support of adequate specific surface area. Conventionally, the specific surface area of the supported catalysts to be used according to the present invention is in the range between 5 and 500 $m^2/g$ (measured with nitrogen by the BET method).

The cobalt content of the supported catalyst is generally between 10 and 70% by weight and preferably between 30 and 50% by weight, based on the supported catalyst. The surface of the support, which is frequently made up of oxide or silicate materials, is partially or essentially completely covered with cobalt, it also being possible for cobalt oxide to be present underneath the surface due to the method of production. Examples of suitable support materials are oxides from the group comprising silicon dioxide, aluminum oxide and titanium dioxide, silicates such as aluminum and calcium silicate, and naturally occurring and synthetically produced zeolites and glass frits. Although commercially available supported catalysts with a high Co content, like catalysts with 50% by weight of Co on aluminum silicate, are being described as essentially completely covered with cobalt, it has been found that catalysts with different supports but with the same specific surface and the same Co content influence the selectivity and the spectrum of side products. Obviously, the surface of the support of the catalyst is at least partially accessible and interferes with the catalytic process.

For reasons of cost, supported catalysts with ruthenium as the catalytically active component generally contain only a small proportion by weight of ruthenium, being generally between 0.5 and 10% by weight and preferably between 2 and 5% by weight.

The production of the above mentioned Co and Ru catalysts, which conventionally comprises impregnation, drying and shaping steps, is known to those skilled in the art; see U.S. Pat. No. 3,352,913 (which is incorporated by reference in its entirety), especially column 2, lines 28–41, and "Heterogeneous Catalysis In Industrial Practice" by Charles N. Satterfield, 2nd edition, 1991, McGraw Hill Inc., chapter 4, pages 87–130 (which is incorporated by reference in its entirety).

It has been established that isophoronediamine is obtainable by the process according to the present invention in higher yield when using a supported cobalt catalyst than when using a supported ruthenium catalyst. This is surprising inasmuch as JP-A 4-300852 and EP-A 0 394 967 have indicated that ruthenium catalysts are particularly effective in the hydrogenation of the nitrile group, which is more difficult to hydrogenate than the carbonyl group.

It is known that isophoronediamine exists in the form of cis and trans isomers (see Die Angewandte Makromolekulare Chemie 153 (1987) 1–13, No. 2502). By studying the isomer ratio of the isophoronediamine prepared according to the present invention, it has been found that the proportion of cis isomer formed is completely predominant when using a ruthenium catalyst: cis/trans isomer ratio according to Example 9 (below) =84 to 16. When using a supported cobalt catalyst, the other conditions being identical, the cis and trans isomers are formed in somewhat equal proportions: cis/trans isomer ratio according to Example 8 (below) =60 to 40.

It has furthermore been found that it is possible to prepare isophoronediamine with a cis/trans isomer ratio above that which is obtainable using a supported cobalt catalyst, and in high yield, by carrying out the aminating hydrogenation reaction in a trickle bed reactor in which an upper layer of a supported ruthenium catalyst and a lower layer of a cobalt fixed bed catalyst are arranged. The cis/trans isomer ratio is dependent upon the reaction temperature and/or the choice of catalyst (see our copending U.S. application corresponding to DE 43 43 891.1); for example, at a temperature of 120° C. (single step temperature method) the cis/trans ratio with a Co-catalyst is between approximately 60 to 40, with a catalyst combination of Ru-Co in dependence from the amount of Ru to Co the cis/trans ratio is from 90 to 10.

Particularly suitable catalysts are ruthenium-on-γ-aluminum oxide and a supported cobalt catalyst with an oxide or silicate support and a cobalt content of 10 to 70% by weight, based on the catalyst. Instead of having one reactor with two layers of different fixed bed catalysts arranged therein, it is also possible to connect two reactors in series, each containing only one fixed bed catalyst; in this case, the first reactor contains the ruthenium fixed bed catalyst and the second reactor contains the cobalt fixed bed catalyst. To obtain a high yield of isophoronediamine with the desired isomer ratio, it is advantageous if the ruthenium fixed bed catalyst, which is positioned first, makes up 3 to 30%, preferably 5 to 20%, of the total catalyst volume.

As explained earlier, the process according to the present invention differs in essential respects from previously known processes, resulting in substantial advantages. By combining the use of a starting mixture of isophoronenitrile, ammonia and an alcoholic solvent with the trickle bed operation of the reactor provided with a fixed bed, it is possible to surprisingly achieve both a high product yield of isophoronediamine and a high selectivity. The formation of undesired by-products, such as methylisophoronediamine, which adversely affects the product quality because it is difficult to separate off, is extensively avoided by the reaction process of the present invention; less than 3000 ppm (preferably 200 ppm or less) of by-products such as methylisophoronediamine are produced. The above mentioned combination of essential features of the present invention is also such that the aminating hydrogenation can be carried out at moderate pressures, thereby greatly reducing the consequent cost of the pressure apparatus compared with the case of a high-pressure apparatus. As it is not necessary according to the present invention to use hydrogen in excess and hence to have to purify and recycle the excess, in contrast to previously known processes using a reactor with a fixed bed catalyst, expensive devices for separating off, purifying and recycling the excess $H_2$ are dispensed with.

Another essential advantage of the process according to the present invention is the unexpectedly long service life of the catalysts, which is attributed to the trickle bed process. Even after several months of operation, no reduction in yield, no change in the range of by-products, and no change in the isomer ratio were found. A further advantage is the ability to obtain isophoronediamine in high yield with a particular isomer ratio, within certain limits.

In the process according to the present invention, there is also no need for a preliminary reaction between isophoronenitrile and ammonia in order to form isophoroneimine, which was considered by the art to be essential for obtaining a high yield and high selectivity in the aminating hydrogenation. In contrast, according to the present invention, a solution of isophoronenitrile in the solvent used is mixed with ammonia directly upstream of the trickle bed reactor and the mixture is fed into the reactor.

The process according to the present invention is illustrated in greater detail with the aid of the following Examples, without implying a limitation.

EXAMPLE 1

A vertical reaction tube is filled with 200 ml of hydrogenation catalyst. The feed solution containing IPN and methanol, and liquid $NH_3$, are pumped into the top of the reactor. Hydrogen also flows into the tube from the top. The reaction temperature is kept at 120° C. by means of oil heating. The pressure is regulated at 6 MPa. The liquid is collected in a separating vessel. The gas stream at the reactor inlet is adjusted so that a gas stream of 100 Nl/h is established downstream of the separating vessel.

The catalyst used was a commercially available solid Co catalyst (ca. 50% Co on silicate support) in the form of extrudates of 4–5 mm in diameter and length. The feed solution contained 24% by weight of IPN and 76% by weight of methanol. 130 ml/h thereof and 70 ml/h of $NH_3$ were mixed directly before being charged into the reactor, and the mixture was pumped into the reactor; the LHSV value was thus 1 $h^{-1}$. According to analysis of the product mixture, the yield of IPDA was 88.7%, based on IPN used. The product mixture also contained 5% of 2-aza-4,6,6-trimethylbicyclo[3,2,1]octane (bicyclic compound) and 4.3% of 3,5,5-trimethyl-6-imino-7-azabicyclo[3,2,1]octane (amidine).

EXAMPLE 2

The experiment was carried out in the same experimental set-up as described in Example 1, except that no gas stream was withdrawn from the separating vessel so only the consumed hydrogen was replaced in order to keep the reaction pressure at 60 bar. The catalyst, liquid streams and liquid composition were the same as described in Example 1.

Analysis of the product mixture of this experiment showed an IPDA yield of 89.2%, based on IPN used The product mixture also contained 4.5% of bicyclic compound and 4.4% of amidine. Surprisingly, an even higher yield of IPDA and a reduction in the "bicyclic" by-product are made possible by the process without excess $H_2$. This experiment was run for 2000 h with no observable loss of yield or change in the range of products.

EXAMPLES 3a and 3b

The experimental set-up used was the same as in Example 1. The hydrogenation pressure was 6 MPa and the reaction temperature was 120° C. The $H_2$ stream was adjusted so that 100 Nl/h of $H_2$ were withdrawn from the separating vessel. The feed solution contained 30% by weight of IPN and 70% by weight of methanol. 130 ml/h thereof were pumped into the reactor together with 50 ml/h of liquid $NH_3$. 200 ml of cobalt catalyst were introduced as the catalyst.

Two processes were studied: In the trickle bed process (3a), gas and liquid flowed through the reactor from top to bottom; in the bubble column process (3b), the reactor was in the flooded state and gas and liquid flowed through it from bottom to top.

A yield of 87.1% was achieved in the trickle bed process (3a). After purification by distillation, the product purity was 99.8%; methyl-IPDA was detectable in an amount of only about 200 ppm.

A yield of 85.5% was achieved in the experiment by the bubble column process (3b). Purification by distillation gave a product purity of only 99.5%. Analysis showed that the pure product still contained 3000 ppm of methyl-IPDA. The methyl-IPDA by-product, which has a very adverse effect on the quality of the IPDA product, is practically inseparable by distillation.

The difference in yield between 3a and 3b is 1.6% which is statistically significant in a commercial process. The difference in purity (3a: 99.8% with 200 ppm methyl-IPDA; 3b: 99.5% with 3000 ppm of methyl-IPDA) is of great practical significance because the methyl-IPDA cannot be separated by distillation. The difference in yield and purity between 3a and 3b shows the unexpected superiority of the present invention over the process of EP-A 0 394 967.

EXAMPLES 4 to 6

These experiments were carried out in the same experimental set-up and under the same reaction conditions as described in Example 1. Only the catalyst was varied. The results are given in the following Table:

| Example | Catalyst | Yield of IPDA (%) |
| --- | --- | --- |
| 4 | 5% Ru/$\gamma$-Al$_2$O$_3$ | 82.1 |
| 5 | Ni | 55.3 |
| 6 | 2% Pd/$\gamma$-Al$_2$O$_3$ | 4 |

Both the Ru and the Pd were applied to $\gamma$-Al$_2$O$_3$ extrudates as the support. Examples 5 and 6 clearly show that the yields obtained with Ni and Pd catalysts are not satisfactory compared with the process according to the present invention.

EXAMPLE 7

The low-boiling components, namely methanol, NH$_3$, H$_2$O and the bicyclic compound, were removed from 8770 g of the reaction solution of Example 2 by fractional distillation. 1292 g of a crude solution remained. 1190 g of IPDA were distilled off from this solution at a bottom temperature of 147° C. and at a pressure of 2 kPa. This corresponds to an isolation yield of 87.3%. 98 g remained as the bottom product of the distillation. A further high-boiling fraction of 74 g was distilled off from this bottom product under reduced pressure (1 kPa) and at a temperature of 162° C. It contained 20% of IPDA and 74% of amidine. This resulting fraction of 74 g corresponds to 5.6% of the amount of IPN used.

In another experiment, which was carried out analogously to Example 2, the high-boiling fraction (i.e., 5.6% based on the amount of IPN used) was added. After hydrogenation and separation of the low-boiling components and purification of the IPDA by distillation, the isolation yield found was 92.3%. Accordingly, it was possible to achieve a 5% increase in the isolation yield of IPDA by recycling the high-boiling fraction containing the amidine.

The yield of IPDA can be increased by a further 4% by catalytically hydrogenating the fraction containing the bicyclic compound (boiling point below that of IPDA) in a separate hydrogenation reactor under elevated temperature conditions (150°–200° C.).

EXAMPLES 8 to 11

The experimental set-up used was the same as in Example 1. The hydrogenation pressure was 60 bar and the reaction temperature was 120° C. No H$_2$ was withdrawn from the separating vessel. The feed solution contained 30% by weight of IPN and 70% by weight of methanol. 130 ml/h thereof were mixed with 50 ml/h of liquid NH$_3$ and pumped into the reactor. This experimental setup was operated with a ruthenium catalyst, a cobalt catalyst and various combinations of the two. The results of this experiment are shown in the following Table:

| Example | Catalyst* | Yield (%) | Isomer ratio cis:trans |
| --- | --- | --- | --- |
| 8 | 200 ml Co | 87.2 | 60:40 |
| 9 | 200 ml Ru | 81.5 | 84:16 |
| 10 | 100 ml Ru + 100 ml Co | 83.7 | 81:19 |
| 11 | 10 ml Ru + 190 ml Co | 86.9 | 78:22 |

*Ru catalyst: 5% Ru on $\gamma$-Al$_2$O$_3$ extrudates; Co catalyst: 50% Co on Al silicate extrudates Use of a Co catalyst alone increases the yield compared to use of a Ru catalyst alone. Use of a Ru catalyst alone increases the cis/trans isomer ratio compared to use of a Co catalyst alone. By combining a Ru catalyst and a Co catalyst, the Ru catalyst being arranged as the upper layer in the reactor, it is possible to obtain IPDA with a high cis/trans isomer ratio in higher yield than by using an Ru catalyst on its own.

EXAMPLE 12

A reaction tube (diameter 16 mm) of a trickle bed hydrogenation apparatus was filled with 120 ml of a commercial Co support catalyst (Co on aluminum silicate, 50% by weight Co; specific surface (BET (N$_2$)) approximately 200 m$^2$/g). The example was performed in a similar manner as Example 1. The reaction temperature was regulated to 110° C., the total pressure (sum of the partial pressures for H$_2$, NH$_3$, methanol) to 6 MPa. The feed solution contained 15% by weight isophoronenitrile, 65% by weight methanol, and 25% by weight ammonia. 100 ml of said feed solution was pumped onto the top of the trickle bed. After trickling of said solution through the trickle bed, the reaction mixture contained (mole % related to isophoronenitrile in the feed solution):

| | |
| --- | --- |
| Isophoronediamine (IPDA) | 89.2% |
| Isophoroneaminoalcohol (IPAA) | 2.1% |
| Amidine compound (see example 1) | 4.0% |
| Bicyclic compound (see example 1) | 3.8% |

EXAMPLE 13

Example 12 was repeated with the only difference in that another commercial Co support catalyst was used (Co on silica, 25% by weight Co, specific surface (BET (N$_2$)) approximately 200 m$^2$/g). The reaction mixture contained (mole % related to isophoronenitrile in the feed solution):

| | |
| --- | --- |
| Isophoronediamine (IPDA) | 87.4% |
| Isophoroneaminoalcohol (IPAA) | 1.2% |
| Amidine compound (see example 1) | 4.3% |
| Bicyclic compound (see example 1) | 5.1% |

Further variations and modifications of the foregoing will be apparent to those skilled in the art and such variations and modifications are attended to be encompassed by the claims that are appended hereto.

What is claimed:

1. A process for the preparation of isophoronediamine from isophoronenitrile, said process comprising charging a reaction mixture of isophoronenitrile, an organic inert solvent, and ammonia onto a catalyst bed at the top end of a trickle bed reactor with hydrogen at a sufficient pressure and at a temperature in the range 80° to 150° C., and withdrawing said reaction mixture after trickling through said catalyst bed at the bottom end of said trickle bed reactor; wherein said catalyst bed contains at least one hydrogenation catalyst selected from the group consisting of cobalt and ruthenium fixed bed catalysts.

2. The process according to claim 1, further comprising working up the reaction mixture by distillation.

3. The process according to claim 1, wherein the LHSV is 0.8–1.5 h$^{-1}$ and said temperature is in the range 90° to 130° C. and said pressure is in the range of 5 to 8 MPa.

4. The process according to claim 1, wherein said temperature is in the range 40° to 150° C. and said pressure is in the range of 3 to 8 MPa.

5. The process according to claim 1, wherein said isophoronenitrile in said solvent is mixed with said ammonia directly upstream of said trickle bed reactor and said mixture is fed into said reactor.

6. The process according to claim 1, wherein said solvent is selected from the group consisting of methanol, ethanol, n-propanol, and isopropanol.

7. The process according to claim 6, wherein said solvent is methanol.

8. The process according to claim 1, wherein said reaction mixture comprises 10 to 40% by weight of isophoronenitrile and 10 to 40% by weight of ammonia and said reaction mixture forms a homogeneous solution.

9. The process according to claim 8, wherein said reaction mixture comprises 10 to 30% by weight of isophoronenitrile and 20 to 40% by weight of ammonia.

10. The process according to claim 1, wherein the LHSV is greater than or equal to 0.5 h$^{-1}$.

11. The process according to claim 10, wherein said LHSV is 0.8–1.5 h$^{-1}$.

12. The process according to claim 1, wherein said hydrogenation catalyst is a supported catalyst consisting essentially of (a) an inorganic support material and (b) 10 to 70% by weight of cobalt or 0.5 to 10% by weight of ruthenium.

13. The process according to claim 12, wherein said hydrogenation catalyst is a supported catalyst consisting essentially of (a) an inorganic support material and (b) 30 to 50% by weight of cobalt or 2 to 5% by weight of ruthenium.

14. The process according to claim 12, wherein said supported catalyst has a BET specific surface area of 5–500 m$^2$/g.

15. The process according to claim 12, wherein said support material is selected from the group consisting of silicon dioxide, aluminum oxide, titanium dioxide, aluminum silicate, calcium silicate, zeolite and glass frit.

16. The process according to claim 1, wherein an excess of hydrogen is not used.

17. The process according to claim 1, wherein said hydrogen is present in an amount required to maintain said pressure.

18. The process according to claim 2, further comprising feeding back into said trickle bed reactor a high-boiling fraction distilling after the isophoronediamine main fraction in the distillative working-up of the reaction mixture.

19. The process according to claim 18, wherein said high-boiling fraction contains 3,5,5-trimethyl-6-imino-7-azabicyclo(3,2,1)octane.

20. The process according to claim 12, wherein said hydrogenation catalyst is a supported catalyst consisting essentially of (a) an inorganic support material and (b) 30 to 50% by weight of cobalt.

21. The process according to claim 1, wherein said trickle bed reactor comprises an upper layer of a supported ruthenium catalyst and a lower layer of a cobalt fixed bed catalyst.

22. The process according to claim 21, wherein said supported ruthenium catalyst is ruthenium-on-γ-aluminum oxide.

23. The process according to claim 21, wherein said cobalt fixed bed catalyst is a supported cobalt catalyst with an oxide or silicate support and a cobalt content of 10 to 70% by weight based on the catalyst.

24. The process according to claim 21, wherein said ruthenium catalyst makes up 3 to 30% of the total catalyst volume.

25. The process according to claim 24, wherein said ruthenium catalyst makes up 5 to 20% of the total catalyst volume.

26. The process according to claim 1, wherein said trickle bed reactor comprises two separate reactors connected in series wherein the first reactor contains a supported ruthenium fixed bed catalyst and the second reactor contains a cobalt fixed bed catalyst.

27. The process according to claim 26, wherein said supported ruthenium catalyst is ruthenium-on-γ-aluminum oxide.

28. The process according to claim 26, wherein said cobalt fixed bed catalyst is a supported cobalt catalyst with an oxide or silicate support and a cobalt content of 10 to 70% by weight based on the catalyst.

29. The process according to claim 26, wherein said ruthenium catalyst makes up 3 to 30% of the total catalyst volume.

30. The process according to claim 29, wherein said ruthenium catalyst makes up 5 to 20% of the total catalyst volume.

31. The process according to claim 1, wherein said process does not involve a preliminary reaction between isophoronenitrile and ammonia in order to form isophoroneimine.

32. The process according to claim 1, wherein said reaction mixture contains at least 10% by weight of isophoronenitrile.

33. The process according to claim 1, wherein said organic inert solvent is a $C_1$- to $C_3$-alcohol.

34. The process according to claim 1, wherein said pressure is in the range 3 to 10 MPa.

35. The process according to claim 1, wherein less than 3000 ppm of methylisophoronediamine is produced.

36. The process according to claim 35, wherein less than or equal to 200 ppm of methylisophoronediamine is produced.

37. The process according to claim 18, wherein the yield of isophoronediamine is greater than 91% to 95%.

38. The process according to claim 1, wherein the yield of isophoronediamine is about 87% to 90%.

39. The process according to claim 38, wherein the yield of isophoronediamine is 87% to 90%.

40. The process according to claim 1, wherein the purity of isophoronediamine is greater than 99.6%.

41. The process according to claim 40, wherein the purity of isophoronediamine is 99.7% to 99.9%.

42. The process according to claim 1, consisting essentially of charging a reaction mixture of isophoronenitrile, an organic inert solvent, and ammonia onto a catalyst bed at the top end of a trickle bed reactor with hydrogen at a sufficient pressure and at a temperature in the range 80° to 150° C., and withdrawing said reaction mixture after trickling through said catalyst bed at the bottom end of said trickle bed reactor; wherein said catalyst bed contains at least one hydrogenation catalyst selected from the group consisting of cobalt and ruthenium fixed bed catalysts.

43. A process for the preparation of isophoronediamine from isophoronenitrile, said process comprising charging a reaction mixture of isophoronenitrile, an organic inert solvent, and ammonia onto a catalyst bed at the top end of a trickle bed reactor with hydrogen at a sufficient pressure and at a temperature in the range 80° to 150° C., and withdrawing said reaction mixture after trickling through said catalyst bed at the bottom end of said trickle bed reactor; wherein said catalyst bed contains at least one hydrogenation catalyst which comprises a cobalt fixed bed catalyst.

44. The process according to claim 43, wherein said hydrogenation catalyst is a supported catalyst consisting essentially of (a) an inorganic support material and (b) 10 to 70% by weight of cobalt.

45. The process according to claim 44, wherein said hydrogenation catalyst is a supported catalyst consisting essentially of (a) an inorganic support material and (b) 30 to 50% by weight of cobalt.

* * * * *